(12) United States Patent
Cullen et al.

(10) Patent No.: US 7,732,655 B2
(45) Date of Patent: *Jun. 8, 2010

(54) CONTROLLED RELEASE THERAPEUTIC WOUND DRESSINGS

(75) Inventors: Breda Mary Cullen, North Yorkshire (GB); Derek Walter Silcock, North Yorkshire (GB); Jonathan Warrick, Issy-les-Moulineaux (FR)

(73) Assignee: Systagenix Wound Management (US), Inc., Wilmington, DE (US)

( * ) Notice: Subject to any disclaimer, the term of this patent is extended or adjusted under 35 U.S.C. 154(b) by 815 days.

This patent is subject to a terminal disclaimer.

(21) Appl. No.: 10/497,442

(22) PCT Filed: Dec. 6, 2002

(86) PCT No.: PCT/GB02/05522

§ 371 (c)(1),
(2), (4) Date: Mar. 3, 2005

(87) PCT Pub. No.: WO03/047643

PCT Pub. Date: Jun. 12, 2003

(65) Prior Publication Data

US 2005/0159695 A1   Jul. 21, 2005

(30) Foreign Application Priority Data

Dec. 6, 2001   (GB) .................................. 0129292.9

(51) Int. Cl.
*A61F 13/00* (2006.01)

(52) U.S. Cl. ......................................... 602/48; 424/433

(58) Field of Classification Search .................. 602/48; 424/433
See application file for complete search history.

(56) References Cited

U.S. PATENT DOCUMENTS 3,800,792 A   4/1974   McKnight et al. ........... 128/156

(Continued)

FOREIGN PATENT DOCUMENTS

EP   0 518 697 A3   12/1992

(Continued)

OTHER PUBLICATIONS

Choi, Y.-S., "Hyaluronic acid and silver sulfadiazine—impregnated polyurethane foams for wound dressing application," *J. of Mat. Sci.*, 2002, 13(9), 861-865.

(Continued)

*Primary Examiner*—Robert A Wax
*Assistant Examiner*—Aradhana Sasan
(74) *Attorney, Agent, or Firm*—Morgan, Lewis & Bockius LLP

(57) ABSTRACT

A wound dressing comprising: a therapeutic agent selected from the group consisting of antimicrobial substances, pain relieving substances, protease inhibitors, and mixtures thereof; and a barrier layer for initially separating the therapeutic agent from a wound fluid in use, wherein the barrier layer comprises a substrate for an enzyme selected from the group consisting of proteases, kallikrein and tissue-plasminogen activator. Preferably the substrate comprises a substrate for elastase or a collagenase. The barrier layer breaks down in infected or chronic wounds, thereby releasing the therapeutic substance selectively into such wounds.

17 Claims, 2 Drawing Sheets

U.S. PATENT DOCUMENTS

Figure 1:
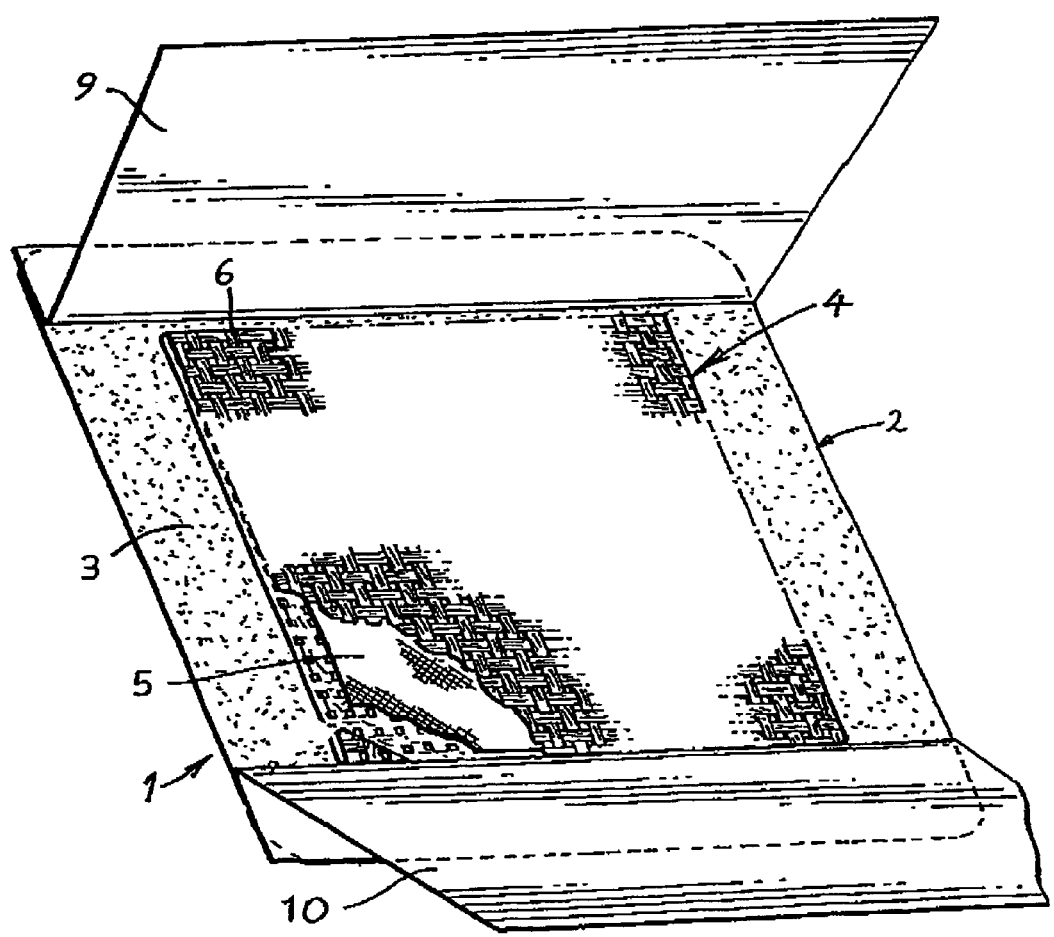

| | | | | |
|---|---|---|---|---|
| 4,060,081 | A | * | 11/1977 | Yannas et al. ............ 623/15.12 |
| 5,196,196 | A | * | 3/1993 | Scott et al. ............... 424/94.64 |
| 5,352,508 | A | | 10/1994 | Cheong ...................... 428/264 |
| 6,117,425 | A | | 9/2000 | MacPhee et al. ......... 424/94.64 |
| 6,160,200 | A | | 12/2000 | Ehrnsperger et al. ........ 604/378 |
| 2006/0111657 | A1 | * | 5/2006 | Addison et al. ............... 602/50 |

FOREIGN PATENT DOCUMENTS

| | | |
|---|---|---|
| EP | 0 541 391 B1 | 6/1998 |
| EP | 0 676 457 B1 | 10/1998 |
| EP | 0 613 692 B1 | 1/1999 |
| EP | 0 599 589 B1 | 2/1999 |
| GB | 1 280 631 | 7/1972 |
| JP | 4-81466 | 3/1992 |
| RU | 2 048 817 C1 | 11/1995 |
| WO | WO 01/15750 A1 | 3/2001 |
| WO | WO 02/38097 A1 | 5/2002 |

OTHER PUBLICATIONS

Choi, Y.-S., et al., "Studies on gelatin—containing artificial skin: II. Preparation and characterization of cross-linked gelatin—hyaluronate sponge," *J. of Biomed. Mat. Res.*, 1999, 48(5), 631-639.

Database WPI, *Derwent Publications Ltd*, London, Section Ch, Week 198826, AN 1988-178826, 1988, XP02233580.

Grzybowski, J., et al., "Biodegradable implants/dressings made of collagen foam and antibiotic for use especially on deep infections by pathogenic microorganisms and method of their preparation," *Chem. Abstracts Ser.*, 2000, Accession No. 134:300841 CA (Abstract).

Grzybowski, J., et al., "Collagen dressings for surface wounds, particularly wounds infected with pathogenic microorganisms and method of the collagen dressing preparation," *Chem. Abstracts Ser.*, 1998, Accession No. 130:276727 CA (Abstract).

Guiot, et al. (Eds.), Polymeric Nanoparticles and Microspheres, *CRC Press*, 1986, Index of Chapters 1-6, 11 pages.

Kornilova, E.G., et al., Database WPI, *Derwent Publications Ltd.*, London, AN 1996-298710, 1996, XP002233581.

Registered Mark PLURONIC, Registration No. 0547988, Registration Date Sep. 11, 1951, 4 pages.

Registered Mark ESTANE 5714F, Registration No. 2533691, Registration Date Jan. 29, 2002, 6 pages.

* cited by examiner

CONTROLLED RELEASE THERAPEUTIC WOUND DRESSINGS

The present invention relates to wound dressing materials, and in particular to new materials for the controlled release of therapeutic agents into wounds.

In mammals, injury triggers an organised complex cascade of cellular and biochemical events that result in a healed wound. Wound healing is a complex dynamic process that results in the restoration of anatomic continuity and function; an ideally healed wound is one that has returned to normal anatomic structure, function and appearance.

Infection of wounds by bacteria delays the healing process, since bacteria compete for nutrients and oxygen with macrophages and fibroblasts, whose activities are essential for the healing of the wound. Infection results when bacteria achieve dominance over the systemic and local factors of host resistance. Infection is therefore a manifestation of a disturbed host/bacteria equilibrium in favour of the invading bacteria. This elicits a systemic septic response, and also inhibits the multiple processes involved in wound healing. Lastly, infection can result in a prolonged inflammatory phase and thus slow healing, or may cause further necrosis of the wound. The granulation phase of the healing process will begin only after the infection has subsided.

Chronically contaminated wounds all contain tissue bacterial flora. These bacteria may be endogenous to the patient or might be exogenous to the wound. Closure, or eventual healing of the wound is often based on a physician's ability to control the level of the bacterial flora.

If clinicians could respond to wound infection as early as possible the infection could be treated topically as opposed to having to use antibiotics. This would also lead to less clinical intervention/hospitalisation and would reduce the use of antibiotics and other complications of infection.

Current methods used to identify bacterial infection rely mainly on judgement of the odour and appearance of a wound. With experience, it is possible to identify an infection in a wound fly certain chemical signs such as redness or pain. Some clinicians take swabs that are then cultured in the laboratory to identify specific organisms, but this technique takes time.

Pain is also associated with infected and chronic wounds. Biochemically, pain is experienced when there is an increase of kinins (bradykinin) in the area of the wound. Kinins are produced by the proteolytic breakdown of kininogen, and the protease responsible for this is kallikrein. Kallikrein also stimulates the production of tissue plasminogen activator (t-PA)

It is also known to provide antimicrobial wound dressings. For example, such dressings, are known having a liquid permeable wound contacting layer, an intermediate absorbent layer and an outer, liquid-impervious backing layer, in which one or more of the layers contains an antimicrobial agent. For example, EP-A-0599589 describes layered wound dressings having a wound contacting layer of a macromolecular hydrocolloid, an absorbent layer, and a continuous, microporous sheet intermediate the wound contacting layer and the absorbent layer. The absorbent layer contains a low molecular weight antimicrobial agent that can diffuse into the wound.

WO-A-0238097 describes wound dressings comprising a liquid-permeable top sheet having a wound facing surface and a back surface, and a hydrogel layer on the wound facing surface of the top sheet The top sheet is adapted to block or restrict passage of liquid from the back surface to the wound facing surface. The hydrogel layer is an insoluble hydrogel adapted to maintain a moist wound healing environment at the wound surface. The hydrogel may contain therapeutic agents such as antimicrobial agents, for sustained release into the wound.

EP-A-0518697 describes a laminated collagen film for delayed release of medicaments. Different layers of the film contain different concentrations of medicaments. The laminated films do not appear to be responsive to wound infection.

U.S. Pat. No. 6,160,200 describes absorbent sanitary articles for absorbing bodily waste. At least a portion of the body facing surface of the articles includes a material capable of dissolving in contact with bodily exudates so as to permit the bodily exudates to pass into an absorbent layer Previous antimicrobial wound dressings suffer from the drawback that the release of the antimicrobial agent is relatively unresponsive to the degree of infection of the wound being treated. This is undesirable because it can result in resistant microorganisms, and also because all unnecessary medication can interfere with the processes of wound healing.

There is thus a need for a wound dressing that will selectively release antimicrobial agents and/or pain relieving agents into infected wounds but not into non-infected wounds, such release into infected wounds taking place preferably even prior to obvious clinical symptoms of infection. Such a dressing would provide early intervention with suitable treatment (e.g. a topical antimicrobial treatment) before wound chronicity sets in.

It has now been discovered that wound fluid from wounds that are apparently not clinically infected but which go on to become infected within a few days have high levels of neutrophil elastase activity and may also have high levels of other inflammatory enzymes, such as macrophage proteases, other neutrophil proteases, bacterial collagenase, plasmin, hyaluronidase, kallikrein or t-PA.

It is known that chronic wounds, such as venous ulcers, pressure sores and diabetic ulcers have a disordered wound healing metabolism even in the absence of infection. In particular, wound chronicity is associated with elevated levels of protease enzymes in the wound that interfere with the normal processes of tissue formation and destruction in the wound.

The present invention provides a wound dressing comprising: a therapeutic agent selected from the group consisting of antimicrobial substances, pain relieving substances, protease inhibitors, and mixtures thereof; and a barrier layer for initially separating the therapeutic agent from a wound fluid in use, wherein the barrier layer comprises a substrate for an enzyme selected from the group consisting of proteases, kallikrein and tissue-plasminogen activator.

The antimicrobial agent may, for example, comprise an antiseptic, an antibiotic, or mixtures thereof. Preferred antibiotics include tetracycline, penicillins, terramycins. erythromycin, bacitracin, neomycin, polymycin B, mupirocin, clindamycin and mixtures thereof. Preferred antiseptics include silver sulfadiazine, chlorhexidine, povidone iodine, triclosan, other silver salts, sucralfate, quaternary ammonium salts and mixtures thereof. The pain relieving agent may be an analgesic or a local anaesthetic.

The barrier layer is separate from the therapeutic agent, and the therapeutic agent is initially prevented from contacting the wound fluid by the barrier layer. That is to say, the bioavailability of the therapeutic agent to the wound surface is preferably initially substantially zero, and remains substantially zero or low for a finite time until the barrier material has been broken down by the enzyme, at which point the bioavailability increases sharply. Since the enzyme levels are elevated in infected or chronic wounds, this provides for accelerated and/or selective release of the therapeutic agent into such wounds. The barrier layer is normally substantially impervious to wound fluid and insoluble therein unless the wound fluid contains a sufficient level of the specified enzyme to break down the substrate material. The barrier layer is preferably substantially free of the therapeutic agents.

The protease may be a macrophage or neutrophil protease, or a human or bacterial collagenase or gelatinase. The macrophage and neutrophil proteases include elastase, matrix metalloproteinase 9 (MMP-9), MMP-8, cathepsin G, MMP-12, capases and mixtures thereof. Suitable substrates for neutrophil elastases and Cathepsin G comprise Elastin, fibronectin, or mixtures thereof. Suitable substrates for collagenases comprise collagen, gelatin, or mixtures thereof. Suitable substrates for plasmin comprise fibrinogen, fibrin, casein, or mixtures thereof. Suitable substrates for MMP's comprise collagen, gelatin, or mixtures thereof. Suitable substrates for hyaluronidases compose hyaluronic acid or salts thereof. Suitable substrates for kallikrein comprise plasminogen, fibrinogen, or mixtures thereof. Suitable substrates for t-PA comprise plasminogen and fibrin.

The barrier layer is preferably about 0.1 to about 3 mm thick. Preferably about 0.5 to 1.5 mm thick. The enzyme substrate material may be combined in a film-forming composition with additional polymeric materials, plasticisers, and humectants. Suitable polymers include alginates, guar gum, carboxymethyl cellulose, methyl cellulose, hydroxypropyl methyl cellulose, locust bean gum, carrageenan, chitosan, heparan sulfate, dermatan sulfate, glycosaminoglycans such as hyaluronic acid, proteoglyrans, and mixtures thereof. Suitable plasticisers include C2-C8 polyhydric alcohols such as glycerol. Preferably the enzyme substrate compounds make up at least about 10% by weight, more preferably at least about 20% by weight of the film-forming composition.

The barrier layer is preferably a flexible sheet that is conformable to the contours of a wound, and preferably the sheet has an area of at least about 1 cm$^2$. In certain embodiments the barrier layer comprises a substantially continuous film comprising the film forming composition of enzyme substrate as described above. In other embodiments the barrier layer comprises an apertured sheet having a composition comprising the substrate material applied thereto in occlusive fashion. The occlusive composition may be similar to the film-forming composition described above. In these embodiments, the apertures typically make up from about 0.1% to about 50% of the area of the wound facing surface of the sheet before swelling, more typically from about 1% to about 30% of the area of the apertured sheet, and preferably from about 10% to about 25% of the area of the apertured sheet. Typically, the apertured sheet has from about 1 to about 30 apertures per square cm, for example from about 4 to about 15 apertures per square cm or from about 5 to about 10 apertures per square cm. In certain embodiments the apertures are uniformly diluted over the surface of the sheet, preferably in a regular pattern. The mean area of each aperture may for example be from about 0.01 to about 10 mm$^2$, preferably from about 0.1 to about 4 mm$^2$, and more preferably from about 1 mm$^2$ to about 2 mm$^2$. It will be appreciated that the sheet may include more than one size and shape of aperture in order to provide apertures that open more or less quickly on exposure to infected wound fluid. This enables still more control over the dynamics of therapeutic agent delivery to the wound. Typically, substantially the whole area of the apertures in the apertured sheet is blocked by the barrier material before exposure to wound exudate Preferably, the thickness of the barrier film or the apertured sheet (by ASTM D374-79) is from about 0.2 to about 5 mm, more preferably from about 0.4 to about 3 mm.

For example, the barrier layer material may further comprise a polymer selected from the group consisting of water soluble macromolecular materials (hydrogels) such as sodium alginate, sodium hyaluronate, alginate derivatives such as the propylene glycol alginate described in EP-A-0613692, and soluble hydropolymers formed from vinyl alcohols, vinyl esters, vinyl ethers and carboxy vinyl monomers, meth(acrylic) acid, acrylamide. N-vinyl pyrrolidone, acylamidopropane sulphonic acid, PLURONIC (Registered Trade Mark) (block polyethylene glycol, block polypropylene glycol) polystyrene-, maleic acid, NN-dimethylacrylamide diacetone acrylamide, acryloyl morpholine, and mixtures thereof. Suitable hydrogels are also described in U.S. Pat. No. 5,352,508.

The barrier layer material may further comprise a polymer selected from the group consisting of bioerodible polymers such as polylactide/polyglycolide, collagen, gelatin, polyacrylate gels such as those described in EP-A-0676457, calcium alginate gels, crosslinked hyaluronate gels, gels of alginate derivatives such as propylene glycol alginate, and gels wherein the hydropolymer is formed from vinyl alcohols, vinyl esters, vinyl ethers and carboxy vinyl monomers, meth(acrylic) acid, acrylamide, N-vinyl pyrrolidone, acylamidopropane sulphonic acid, PLURONIC (Registered Trade Mark) (block polyethylene glycol, block polypropylene glycol) polystyrene-, maleic acid, NN-dimethylacrylamide diacetone acrylamide, acryloyl morpholine, and mixtures thereof. Suitable hydrogels are also described in U.S. Pat. No. 5,352,508.

The barrier layer material may further comprise from about 5 to about 50% by weight, preferably from 16 to 40% by weight, on the same basis of one or more humectants such as glycerol. The barrier layer material may further contain up to about 30% w/w, more preferably up to about 15% w/w on the same basis of water.

In certain embodiments wound dressings have a layered structure wherein preferably a layer of the antimicrobial substance is provided behind the barrier layer. That is to say, on the side of the barrier layer opposite to the wound facing surface of the barrier layer in use. The layer of antimicrobial substance may contact the barrier layer directly, or may be separated therefrom for example by an absorbent layer.

Preferably, the barrier sheet according to these embodiments of the invention forms part of a layered wound dressing having the antimicrobial material disposed on the side of the barrier sheet opposite to the wound facing side of the barrier sheet Preferably, the layered wound dressing further comprises an absorbent layer and/or a backing layer.

The area of the optional absorbent layer is typically in the range of from 1 cm$^2$ to 200 cm$^2$, more preferably from 4 cm$^2$ to 100 cm$^2$.

The optional absorbent layer may be any of the layers conventionally used for absorbing wound fluids, serum or blood in the wound healing art, including gauzes, nonwoven fabrics, superabsorbents, hydrogels and mixtures thereof. Preferably, the absorbent layer comprises a layer of absorbent foam, such as an open celled hydrophilic polyurethane foam prepared in accordance with EP-A-0541391. the entire content of which is expressly incorporated herein by reference. In other embodiments, the absorbent layer may be a nonwoven fibrous webs for example a carded web of viscose staple fibers. The basis weight of the absorbent layer may be in the range of 50-500 g/m$^2$, such as 100-400 g/m$^2$. The uncompressed thickness of the absorbent layer may be in the range a from 0.5 mm to 10 mm, such as 1 mm to 4 mm. The free (uncompressed) liquid absorbency measured for physiological saline may be in the range of 5 to 30 g/g at 25°. In certain embodiments the antimicrobial material may be dispersed in or on the absorbent layer.

Preferably the dressing further comprises a backing layer covering the barrier sheet and the optional absorbent layer on the side opposite the wound-facing side of the dressing. The backing layer preferably provides a barrier to passage of microorganisms through the dressing and further preferably blocks the escape of wound fluid from the dressing. The backing layer may extend beyond at least one edge of the barrier sheet and optional absorbent layer to provide an adhesive-coated margin adjacent to the said edge for adhering the dressing to a surface, such as to the skin of a patient adjacent to the wound being treated. An adhesive-coated margin may extend around all sides of the barrier sheet and optional absorbent layer, so that the dressing is a so-called island dressing. However, it is not necessary for there to be any adhesive-coated margin.

Preferably, the backing layer is substantially liquid-impermeable. The backing sheet is preferably semi-permeable. That is to say, be backing sheet is preferably permeable to water vapour, but not permeable to liquid water or wound exudate. Preferably, the backing sheet is also microorganism-impermeable. Suitable continuous conformable backing sheets will preferably have a moisture vapor transmission rate (MVTR) of the backing sheet alone of 300 to 5000 $g/m^2/24$ hrs, preferably 500 to 2000 $g/m^2/24$ hrs at 37.5 C at 100% to 10% relative humidity difference. The backing sheet thickness is preferably in the range of 10 to 1000 micrometers, more preferably 100 to 500 micrometers.

Suitable polymers for forming the backing sheet include polyurethanes and poly alkoxyalkyl acrylates and methacrylates such as those disclosed in GB-A-1280631. Preferably, the backing sheet comprises a continuous layer of a high density blocked polyurethane foam that is predominantly closed-cell. A suitable backing sheet material is the polyurethane film available under the Registered Trade Mark ESTANE 5714F.

The adhesive layer (where present) should be moisture vapor transmitting and/or patterned to allow passage of water vapor therethrough. The adhesive layer is preferably a continuous moisture vapor transmitting, pressure sensitive adhesive layer of the type conventionally used for island-type wound dressings, for example, a pressure sensitive adhesive based on acrylate ester copolymers, polyvinyl ethyl ether and polyurethane as described for example in GB-A-1280631. The basis weight of the adhesive layer is preferably 20 to 250 $g/m^2$, and more preferably 50 to 150 $g/m^2$. Polyurethane-based pressure sensitive adhesives are preferred.

Preferably, the adhesive layer extends outwardly form the absorbent layer and the envelope to form an adhesive-coated margin on the backing sheet around the absorbent layer as in a conventional island dressing.

Also within the scope of the present invention are embodiments in which the barrier layer substantially encapsulates the antimicrobial substance. For example, the dressing may comprise, or consist essentially of, particles such as microspheres of antimicrobial material encapsulated in a layer comprising the substrate material. The particles are preferably loaded with from 1 to 90 wt. %, more preferably from 3 to 50 wt. % of the antimicrobial agents.

The particles may be made by any suitable technique, including comminution, coacervation, or two-phase systems for example as described in U.S. Pat. No. 3,886,084. Techniques for the preparation of medicated microspheres for drug delivery are reviewed, for example, in *Polymeric Nanoparticles and Microspheres*, Gulot and Couvreur eds., CRC Press (1986).

A preferred method for preparation of the microparticles is coacervation, which is especially suited to the formation of particles in the preferred size range of 100 to 500 micrometers having a high loading of therapeutic agents. Coacervation is the term applied to the ability of a number of aqueous solutions of colloids, to separate into two liquid layers, one rich in colloid solute and the other poor in colloid solute. Factors which influence this liquid-liquid phase separation are: (a) the colloid concentration, (b) the solvent of the system, (c) the temperature, (d) the addition of another polyelectrolyte, and (e) the addition of a simple electrolyte to the solution. Coacervation can be of two general types. The first is called "simple" or "salt" coacervation where liquid phase separation occurs by the addition of a simple electrolyte to a colloidal solution. The second is termed "complex" coacervation where phase separation occurs by the addition of a second colloidal species to a first colloidal solution, the particles of the two dispersed colloids being oppositely charged. Generally, materials capable of exhibiting an electric charge in solution (i.e. materials which possess an ionizable group) are coacervable. Such materials include natural and synthetic macromolecular species such as gelatin, acacia, tragacanth, styrene-maleic anhydride copolymers, methyl vinyl ether-maleic anhydride copolymers, polymethacrylic acid, and the like.

If, prior to the initiation of coacervation, a water-immiscible material, such as an oil, is dispersed as minute droplets in an aqueous solution or sol or an encapsulating colloidal material, and then, a simple electrolyte, such as sodium sulfate, or another, oppositely charged colloidal species is added to induce coacervation, the encapsulating colloidal material forms around each oil droplet, thus investing each of said droplets in a liquid coating of the coacervated colloid. The liquid coatings which surround the oil droplets must hereafter be hardened by cross-linking to produce solid-walled microcapsules Preferably, the wound dressing according to any aspect of the present invention is sterile and packaged in a microorganism-impermeable container.

Figure 2:
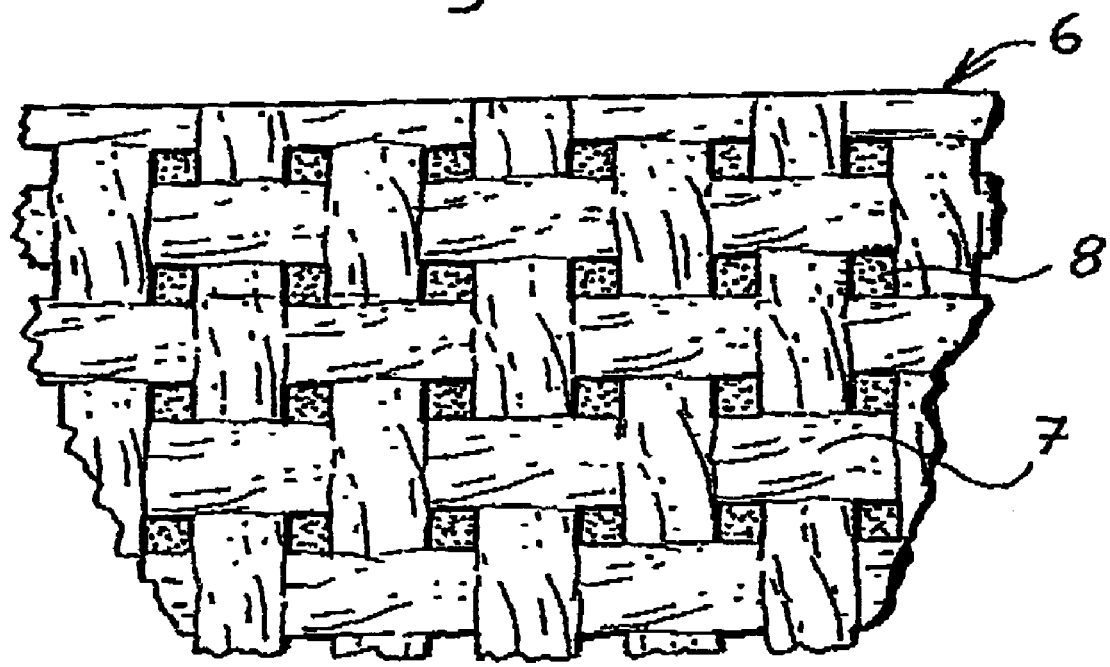

An embodiment of the present invention will now be described further, by way of example, with reference to the accompanying drawings, in which:

FIG. 1 shows a perspective view of the lower (wound contacting) surface of a wound dressing according to the invention with the wound contacting sheet according to the invention partially cut away; and FIG. 2 shows a plan view of a portion of the wound contacting sheet according to the invention from the dressing of FIG. 1.

Referring to FIG. 1, the wound dressing 1 is an island-type self-adhesive wound dressing comprising a backing layer 2 of microporous liquid-impermeable polyurethane foam, such as ESTANE 5714F (Registered Trade Mark). The backing layer is permeable to water vapor, but impermeable to wound exudate and microorganisms.

The backing layer 2 is coated with a substantially continuous layer 3 of pressure sensitive polyurethane adhesive. An absorbent island 4 continuing the antimicrobial is adhered to a central region of the adhesive-coated backing sheet 2.

The absorbent island 4 comprises an absorbent layer 5 of gauze having a basis weight of about 250 $g/m^2$ and impregnated with silver sulfadiazine in an amount of about 25 /$m^2$.

A wound contacting barrier sheet 6 extends over the absorbent layer 5 and is wrapped around the absorbent layer 5, and adhered to the backing layer 2 behind the absorbent layer 5 by the adhesive 3. The wound contacting sheet 6 consists of a support layer 7 of a perforated polypropylene film with 12 perforations per cm² in which the apertures 8 are occluded by a collagenase-degradable film composition prepared as follows.

1 g of collagen fibers formed by freeze drying Type I collagen extracted from limed bovine hide were suspended in 100 ml of 0.05M acetic acid. 40 ml of this suspension was poured into a 10 cm×10 cm square plastic dish. The dish was placed in a drying cabinet at room temperature until be weight of the container had reduced to 50% of the initial weight. At this stage the perforated polypropylene film with 12 perforations per cm² was placed on the surface of the collagen suspension. The suspension was then fully dried and peeled from the square dish. The resulting material had the apertures of the polypropylene film occluded by a thin film of Type I collagen.

The wound facing surface of the dressing shown in FIG. 1 is protected by two silicon-coated release papers 9,10. The dressing is packaged in a microorganism-impermeable pouch (not shown), and sterilised using gamma radiation.

In use, the dressing 1 is removed from the package, the release papers 9,10 are removed, and the dressing is adhered to the skin around the wound by the adhesive layer 3, with the wound contacting sheet in contact with the wound to provide a sterile and absorbent dressing. The dissolution of the collagen in the presence of elevated levels of collagenase triggers the release of antimicrobial active agent from the absorbent layer into the wound in response to increased collagenase production by infected or chronic wounds. This has the further benefit of allowing excess exudate to escape through the perforated sheet 7 into the absorbent layer 5.

The above embodiment has been described by way of example only. Many other embodiments falling within the scope of the accompanying claims will be apparent to the skilled reader.

The invention claimed is:

1. A wound dressing comprising:
   a therapeutic agent selected from the group consisting of antimicrobial substances, pain relieving substances, protease inhibitors, and mixtures thereof; and
   a wound contacting barrier layer for initially separating the therapeutic agent from a wound fluid, said barrier layer comprising a substrate for an enzyme from an infected or chronic wound selected from the group consisting of proteases, kallikrein and tissue-plasminogen activator,
   wherein said barrier layer is substantially free of the therapeutic agent, is substantially impervious to and insoluble in wound fluid free of said enzyme and, in use, separates said therapeutic agent from said wound fluid until and unless said substrate is broken down by said enzyme from an infected or chronic wound.

2. The wound dressing according to claim 1, wherein the therapeutic substance comprises an antiseptic, an antibiotic, an analgesic, a local anaesthetic, a protease inhibitor, or mixtures thereof.

3. The wound dressing according to claim 2, wherein the therapeutic substance comprises an antiseptic selected from the group consisting of chlohexidine, silver sulfadiazine, povidone iodine, silver salts, triclosan, sucralfate, quaternary ammonium salts, and mixtures thereof.

4. The wound dressing according to claim 2, wherein the therapeutic substance comprises an antibiotic selected from the group consisting of tetracycline, penicillins, terramycins, erythromycin, bacitracin, neomycin, polymycin B, mupirocin, clindamycin and mixtures thereof.

5. The wound dressing according to claim 1, further comprising a liquid-impermeable backing layer over the therapeutic substance and the barrier layer.

6. The wound dressing according to claim 5, wherein the backing layer is adhesive-coated and provides an adhesive-coated margin around the therapeutic substance and the barrier layer.

7. The wound dressing according to claim 1, further comprising an absorbent layer.

8. The wound dressing according to claim 1, wherein the barrier layer comprises a substantially continuous film comprising the substrate material.

9. The wound dressing according to claim 1, wherein the barrier layer comprises an apertured sheet having a composition comprising the substrate material applied thereto in occlusive fashion.

10. The wound dressing according to claim 8 or 9, wherein a layer of the therapeutic substance is provided behind the barrier layer.

11. The wound dressing according to claim 10, wherein an absorbent layer is provided behind the barrier layer and the therapeutic substance is dispersed in the absorbent layer.

12. The wound dressing according to any one of claims 1 to 7, wherein the barrier layer substantially encapsulates the therapeutic substance.

13. The wound dressing according to any one of claims 1 to 9, wherein the substrate material comprises a substance selected from the group consisting of elastin, fibronectin, collagen, crossliniked gelatin, fibrinogen, casein, hyaluronic acid, plasminogen, fibrin, and mixtures thereof.

14. The wound dressing according to claim 10, wherein the substrate material comprises a substance selected from the group consisting of elastin, fibronectin, collagen, crossliniked gelatin, fibrinogen, casein, hyaluronic acid, plasminogen, fibrin, and mixtures thereof.

15. The wound dressing according to claim 11, wherein the substrate material comprises a substance selected from the group consisting of elastin, fibronectin, collagen, crossliniked gelatin, fibrinogen, casein, hyaluronic acid, plasminogen, fibrin, and mixtures thereof.

16. The wound dressing according to claim 12, wherein the substrate material comprises a substance selected from the group consisting of elastin, fibronectin, collagen, crossliniked gelatin, fibrinogen, casein, hyaluronic acid, plasminogen, fibrin, and mixtures thereof.

17. A method for treating a wound, comprising providing a wound dressing according to claim 1, and topically applying it to a wound.

* * * * *